US012416087B2

(12) United States Patent
Goto et al.

(10) Patent No.: US 12,416,087 B2
(45) Date of Patent: Sep. 16, 2025

(54) METHOD FOR PRODUCING METAL CARBIDE, METHOD FOR PRODUCING HYDROCARBON, AND METAL CARBIDE COMPOSITION

(71) Applicants: THE DOSHISHA, Kyoto (JP); DAIKIN INDUSTRIES, LTD., Osaka (JP)

(72) Inventors: Takuya Goto, Kyotanabe (JP); Takashi Watanabe, Kyotanabe (JP); Yuta Suzuki, Kyotanabe (JP); Haruka Fukuda, Kyotanabe (JP); Atsuya Yamada, Kyotanabe (JP); Tomohiro Isogai, Osaka (JP); Yosuke Kishikawa, Osaka (JP); Akiyoshi Yamauchi, Osaka (JP)

(73) Assignees: THE DOSHISHA, Kyoto (JP); DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 18/623,692

(22) Filed: Apr. 1, 2024

(65) Prior Publication Data

US 2024/0240332 A1 Jul. 18, 2024

Related U.S. Application Data

(63) Continuation of application No. PCT/JP2022/037024, filed on Oct. 3, 2022.

(30) Foreign Application Priority Data

Oct. 4, 2021 (JP) ................................ 2021-163670

(51) Int. Cl.

*C25B 9/09* (2021.01)
*C25B 1/01* (2021.01)
(Continued)

(52) U.S. Cl.

CPC ................. *C25B 9/09* (2021.01); *C25B 1/01* (2021.01); *C25B 3/03* (2021.01); *C25B 3/26* (2021.01)

(58) Field of Classification Search

None
See application file for complete search history.

(56) References Cited

U.S. PATENT DOCUMENTS 4,009,219 A 2/1977 Tamers
4,137,295 A 1/1979 Tamers
(Continued)

FOREIGN PATENT DOCUMENTS

EP 4394085 A1 7/2024
JP 61-178412 A 8/1986
(Continued)

OTHER PUBLICATIONS

Xinxin Liang et al., "Electrochemical Reduction of Carbon Dioxide and Iron Oxide in Molten Salts to Fe/Fe3C Modified Carbon for Electrocatalytic Oxygen Evolution", Angewandte Chemie, Jan. 18, 2021, vol. 133, No., 4, pp. 2148-2152, 5 total pages.
(Continued)

*Primary Examiner* — Wojciech Haske
(74) *Attorney, Agent, or Firm* — Sughrue Mion, PLLC

(57) ABSTRACT

A method for producing a hydrocarbon including: preparing a molten salt containing a carbonate of a first metal; obtaining precipitates containing a first metal carbide by applying a voltage to the molten salt; and obtaining a gas containing the hydrocarbon and a hydroxide of the first metal by hydrolyzing the first metal carbide.

4 Claims, 9 Drawing Sheets

START

PREPARE MOLTEN SALT CONTAINING CARBONATE OF FIRST METAL — S11

APPLY VOLTAGE (PRECIPITATION OF FIRST METAL CARBIDE) — S12

END

(51) Int. Cl.

| | |
|---|---|
| ***C25B 3/03*** | (2021.01) |
| ***C25B 3/26*** | (2021.01) |

(56) References Cited

U.S. PATENT DOCUMENTS

| | | | |
|---|---|---|---|
| 7,494,637 | B2 | 2/2009 | Peters et al. |
| 2018/0044183 | A1 | 2/2018 | Licht et al. |

FOREIGN PATENT DOCUMENTS

| | | | |
|---|---|---|---|
| JP | H02-256626 | A | 10/1990 |
| JP | 2018-035328 | A | 3/2018 |
| JP | 2018-513911 | A | 5/2018 |

OTHER PUBLICATIONS

D.C. Topor et al., “Molybdenum Carbide Coatings Electrodeposited from Molten Fluoride Bath”, Journal of the Electrochemical Society, Feb. 1988, vol. 135, No. 2, pp. 384-387, 6 total pages.
Hideki Yabe et al., “The Effect of Silver Ion on Electrodeposition of Tungsten and Tungsten Carbide From Molten Chloride”, Electrochimica Acta, Jan. 1990, vol. 35, No. 1, pp. 187-189, 3 total pages.
International Search Report for International Application No. PCT/JP2022/037024 dated Dec. 20, 2022.
International Preliminary Report on Patentability (with translation of Written Opinion) dated Apr. 9, 2024, issued in International Application No. PCT/JP2022/037024.
Communication dated Mar. 19, 2025 issued by the European Patent Office in application No. 22878489.8.

METHOD FOR PRODUCING METAL CARBIDE, METHOD FOR PRODUCING HYDROCARBON, AND METAL CARBIDE COMPOSITION

CROSS REFERENCE TO RELATED APPLICATIONS

This application is a Rule 53(b) Continuation of International Application No. PCT/JP2022/037024 filed Oct. 3, 2022, claiming priority based on Japanese Patent Application No. 2021-163670 filed Oct. 4, 2021, the disclosures of which are incorporated herein by reference in their respective entireties

TECHNICAL FIELD

The present invention relates to a method for producing a metal carbide, a method for producing a hydrocarbon, and a metal carbide composition.

BACKGROUND ART

Acetylene is an industrially important substance as a raw material for various organic compounds. Acetylene is usually obtained by the reaction of a metal carbide (mainly calcium carbide) and water.

Calcium carbide is generally obtained by heating a mixture of quicklime (calcium oxide) and coke to a high temperature in an electric furnace (for example, Patent Document 1). Patent Document 2 proposes that the coke is briquetted in advance and mixed with quicklime. According to Patent Document 2, calcium carbide can be obtained thereby more effectively. Patent Document 3 proposes a method for producing lithium carbide by reacting metallic lithium obtained by melting and electrolyzing lithium chloride with carbon powder such as carbon black. Patent Document 4 proposes a method for producing carbon nanofibers by electrolyzing a molten carbonate.

PRIOR ART DOCUMENTS

Patent Documents

Patent Document 1: JP 61-178412 A
Patent Document 2: JP 2018-35328 A
Patent Document 3: JP 2-256626 A
Patent Document 4: JP 2018-513911 A

SUMMARY

The present disclosure includes the following embodiments.

A method for producing a metal carbide, comprising: preparing a molten salt containing a carbonate of a first metal; and obtaining precipitates containing a first metal carbide by applying a voltage to the molten salt.

Effects

The present disclosure provides a method for producing a metal carbide using metal carbonate as a metal source, a method for producing a hydrocarbon from the metal carbide obtained using metal carbonate as a metal source, and a metal carbide composition.

DESCRIPTION OF EMBODIMENTS

In the method for producing a metal carbide of the present disclosure, a voltage is applied to a molten salt containing a metal carbonate. This method using molten salts allows the reaction to proceed rapidly and efficiently at relatively low temperatures below 800° C. to obtain metal carbide. Furthermore, the target metal carbide can be obtained with higher productivity, selectivity, and safety since a metal carbonate is used. In addition, a carbonate such as calcium carbonate, whose applications are limited, can be utilized effectively. Since a metal carbonate is obtained by fixing carbon dioxide to a metal, $CO_2$, which is said to be a cause of global warming, can be utilized effectively.

The present disclosure includes obtaining a hydrocarbon by hydrolyzing the metal carbide obtained by the aforementioned method. This method can efficiently obtain high-purity hydrocarbons.

The present disclosure includes: reacting a metal hydroxide produced as a by-product in hydrolysis of a metal carbide with carbon dioxide to reproduce a metal carbonate; and reusing it as a metal source for producing the aforementioned metal carbide. This creates a recycling system that includes the production of a first metal carbide using a carbonate of a first metal and the production of a hydrocarbon using the first metal carbide. Resources and $CO_2$, which is said to be the cause of global warming, can be utilized effectively. The method of the present disclosure is very useful, from the perspective of environmental conservation.

The present disclosure includes a carbide composition containing a carbide of the first metal. This carbide composition can be utilized for producing a hydrocarbon.

[Method for Producing Metal Carbide]

Figure 1:
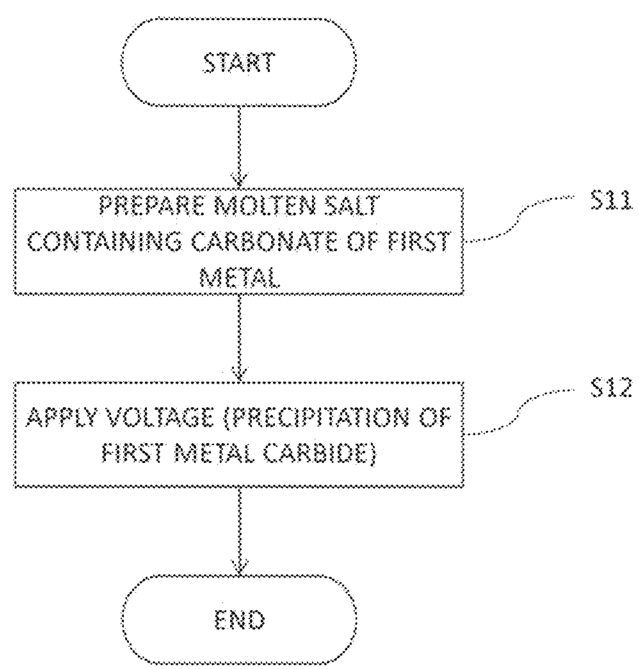
FIG. 1 is a flowchart showing a method for producing a metal carbide according to the present disclosure.

The method for producing a metal carbide according to the present disclosure comprises: preparing a molten salt containing a carbonate of a first metal; and applying a voltage to the molten salt, to obtain precipitates containing a carbide of the first metal. FIG. 1 is a flowchart showing the method for producing a metal carbide according to the present disclosure.

(I) Preparation of Molten Salt (S11)

First, a molten salt containing a carbonate of a first metal is prepared. The carbonate of the first metal is the metal source of the target metal carbide. For convenience of description, a metal salt (including a metal oxide) contained in the electrolytic bath will be referred to as a molten salt, if it is not completely ionized.

(Carbonate of First Metal)

The carbonate of the first metal is not limited and is appropriately selected depending on the target metal carbide. The first metal is preferably at least one selected from the group consisting of alkali metals and alkaline earth metals. Alkali metals and alkaline earth metals have lower ionization energy than other metals and are more easily ionized.

Examples of the alkali metals include at least one selected from the group consisting of lithium (Li), sodium (Na), potassium (K), rubidium (Rb), cesium (Cs), and francium (Fr). Preferable examples of the alkali metals include at least one selected from the group consisting of Li, Na, K, Rb, and Cs. At least one selected from the group consisting of Li, Na, K, and Cs is preferable.

Examples of the alkaline earth metals include at least one selected from the group consisting of beryllium (Be), magnesium (Mg), calcium (Ca), strontium (Sr), barium (Ba), and radium (Ra). Preferable examples of the alkaline earth metals include at least one selected from the group consisting of Mg, Ca, Sr, and Ba.

In consideration of the solubility of the carbonate of the first metal with water, Li, Na, K, Rb and Cs are preferable as the first metal. Na and Ca are more preferable in terms of low cost, and Li and Ca are more preferable in terms of reactivity.

Li, Na, K, and Cs are preferable as the first metal for high solubility of the hydroxide in water. The high solubility of the hydroxide of the first metal in water enhances the recycling efficiency of the first metal in the subsequent step. In the method for producing a hydrocarbon, the metal carbide is hydrolyzed and the hydroxide of the first metal is produced as a by-product together with the hydrocarbon. Hydrocarbons are generally difficult to dissolve in water, they can be easily extracted as a gas. Carbon contained in the precipitates is suspended or settled in water. When the hydroxide of the first metal as a by-product is dissolved in water, carbon can be removed by filtration efficiently. The hydroxide of the first metal can be recovered by removing water from the filtrate. The hydroxide of the first metal is reacted with carbon dioxide, and the carbonate of the first metal is obtained. The higher the solubility of the hydroxide of the first metal in water, the easier the carbonate of the first metal can be recovered. The carbonate of the first metal obtained is reused for preparing the aforementioned molten salt. Meanwhile, the lower the solubility of the hydroxide of the first metal in water, the lower the energy required for its recover. For reducing the energy, the first metal is preferably Ca.

The amount of the carbonate of the first metal contained in the molten salt is not limited. In view of the reaction efficiency, the number of moles of the carbonate of the first metal is preferably 1 mol % or more, more preferably 2 mol % or more, particularly preferably 3 mol % or more, relative to the total number of moles of the molten salt in the electrolytic bath. The larger the number of moles of the carbonate of the first metal, the more preferable it is, in view of the reaction efficiency, but when the melting point of the molten salt is excessively increased, another metal salt may be appropriately mixed. In one embodiment, the number of moles of the carbonate of the first metal is 1 mol % or more, or may be 100 mol %, relative to the total number of moles of the molten salt in the electrolytic bath.

(Other Metal Salt)

The molten salt preferably contains a molten salt of a metal salt other than the carbonate of the first metal. The molten salt of the other metal salt mainly functions as an electrolyte in the electrolytic bath. Also, the other metal salt facilitates melting of the carbonate of the first metal. Examples of the other metal salt include a salt of ions of a metal (hereinafter referred to as second metal) and their counter ions (hereinafter referred to as second anions).

The second metal and the first metal may be the same or different. When the second metal is the same as the first metal, the carbide of the first metal is easily generated. When the second metal is the same as the first metal, the second anion is other than carbonate ions.

The other metal salt is not limited, as long as the metal carbide that is a target substance can be stably precipitated. The other metal salt is preferably melted at a temperature of 800° C. or less.

Examples of the second metal include alkali metals, alkaline earth metals, rare earth elements, aluminum (Al), gallium (Ga), indium (In), thallium (TI), zinc (Zn), cadmium (Cd), gold (Au), silver (Ag), and copper (Cu). The alkali metal and the alkaline earth metal are as described above. Examples of the rare earth element include scandium (Sc), yttrium (Y), the lanthanoid element, and the actinoid element. At least one selected from the group consisting of alkali metals and alkaline earth metals is preferable since the melting temperature of the other metal salt tends to be low.

Examples of the second anion include carbonate ions ($CO_3^{2-}$), sulfate ions, phosphate ions, nitrate ions, acetate ions, carboxylate ions, oxide ions ($O_2^-$), and halogen ions. Halogen ions are preferable since the melting temperature of the other metal salts tends to be low. Halogens have a large electron affinity.

Examples of the halogens include at least one selected from the group consisting of fluorine (F), chlorine (Cl), bromine (Br), iodine (I), and astatine (At). Preferable examples of the halogens include at least one selected from the group consisting of F, Cl, Br, and I. F and/or Cl is preferable. F is preferable since the solubility of the carbonate of the first metal can be improved.

The second anion may include carbonate ions, since they can be a carbon source. Preferable examples of the carbonate of the second metal include a carbonate of at least one metal selected from the group consisting of alkali metals and alkaline earth metals that are different from the first metal.

Specific examples of the other metal salts include alkali metal halides such as LiF, NaF, KF, RbF, CsF, LiCl, NaCl, KCl, RbCl, CsCl, LiBr, NaBr, KBr, RbBr, CsBr, Lil, NaI, KI, RbI, and CsI; alkaline earth metal halides such as $MgF_2$, $CaF_2$, $SrF_2$, $BaF_2$, $MgCl_2$, $CaCl_2$), $SrCl_2$, $BaCl_2$, $MgBr_2$, $CaBr_2$, $SrBr_2$, $BaBr_2$, $MgI_2$, $CaI_2$, $SrI_2$, and $BaI_2$; rare earth element halides such as $AlCl_3$; metal oxides such as $Li_2O$ and CaO; carbonates of metals other than the first metal such as $Li_2CO_3$, $Na_2CO_3$, and $K_2CO_3$; and metal nitrates such as $LiNO_3$, $NaNO_3$, and $KNO_3$. At least one selected from the group consisting of lithium salt, sodium salt, and potassium salt is preferable. Chlorides and/or fluorides of at least one selected from the group consisting of Li, Na, and K are more preferable.

One of the other metal salts may be used alone, or two or more of them may be used in combination. It is preferable to use two or more other metal salts in combination since the melting temperature is easily reduced. Examples include combinations of a plurality of chlorides, combinations of a plurality of fluorides, and combinations of one or more chlorides and one or more fluorides. Specific examples include a combination of LiCl and KCl, a combination of LiCl, KCl, and $CaCl_2$), a combination of LiF, NaF, and KF, a combination of NaF and NaCl, and a combination of NaCl, KCl, and $AlCl_3$.

In the combination of a plurality of metal salts, the compounding ratio of the metal salts is not limited. For example, in the combination of NaF and NaCl, the number of moles of NaF may be 10 mol % or more, or 20 mol % or more, relative to the total number of moles of NaF and NaCl. The number of moles of NaF may be 55 mol % or less, 50 mol % or less, or 45 mol % or less, relative to the total number of moles of NaF and NaCl. In one embodiment, the number of moles of NaF is 10 mol % or more and 55 mol % or less, relative to the total number of moles of NaF and NaCl.

(II) Application of Voltage (S12)

Subsequently, a voltage is applied to the molten salt. This results in the reduction of $CO_3^{2-}$ and precipitates containing the carbide of the first metal (first metal carbide) are obtained. Precipitates containing the first metal carbide are precipitated on the surface of an electrode (cathode) having a low potential. Carbon and oxygen may be generated on the cathode as by-products.

When the first metal is Na, sodium carbide ($Na_2C_2$) is precipitated on the cathode as the first metal. On the cathode, carbon and metallic sodium can be also generated.

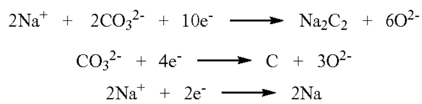

Also when the first metal is Li, K, or Ca, lithium carbide ($Li_2C_2$), potassium carbide ($K_2C_2$), or calcium carbide ($CaC_2$) is precipitated by a similar reaction. The same applies to other first metals.

$O_2^-$ is oxidized on the anode to generate oxygen. The oxygen generated on the anode is exhausted into the gas phase. The oxygen gas can be recovered and used for other applications.

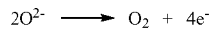

The voltage is applied at a temperature at which the molten salt can be maintained in a molten state. The temperature of the electrolytic bath may be, for example, 150° C. or more, or may be 250° C. or more. The temperature of the electrolytic bath may be, for example, 800° C. or less, or may be 700° C. or less. In the present disclosure, the reaction proceeds at such a relatively low temperature, and thus the energy efficiency is high.

The applied voltage is set so that the cathode potential is between the potential at which carbon is precipitated (Ec) and the potential at which the first metal is precipitated (Em). This can improve the selectivity of the first metal carbide. When the potential of the cathode is excessively high (noble), carbon is mainly precipitated, and the amount of the target first metal carbide generated tends to decrease. When the potential of the cathode is excessively low (base), although the first metal carbide is generated, the metal with the noblest redox potential in the molten salt among the metals contained in the molten salt is mainly precipitated. When a plurality of metals having similar redox potentials in the molten salt are present in the molten salt, alloys of a plurality of metals may be precipitated. For example, when the molten salt contains LiCl, KCl, and $Li_2O$ (5 mol %), the cathode potential may be 0.0 V or more and 1.0 V or less ($Li^+$/Li standard). The voltage may be direct current, intermittent (pulse electrolysis), or superimposed alternating current. The potentials Ec and Em can be determined in the molten salt used, for example, by performing cyclic voltammetry using Ni electrodes.

The material of the cathode is not limited. Examples of the material of the cathode include metals such as Ag, Cu, Ni, Pb, Hg, TI, Bi, In, Sn, Cd, Au, Zn, Ga, Ge, Fe, Pt, Pd, Ru, Ti, Cr, Mo, W, V, Nb, Ta, Zr, and their alloys, and carbon materials such as glassy carbon, natural graphite, isotropic graphite, pyrolytic graphite, plastic formed carbon, and electrically conductive diamond.

The material of the anode is not limited. Examples of the material of the anode include Pt, electrically conductive metal oxide, glassy carbon, natural graphite, isotropic graphite, pyrolytic graphite, plastic formed carbon, and conductive diamond. Examples of the electrode made of electrically conductive metal oxide include a transparent electrically conductive electrode formed into a film using a mixed oxide of indium and tin on glass, which is called ITO electrode, an electrode formed into a film of the oxide of a platinum group-metal such as ruthenium and iridium on a substrate such as titanium, which is called DSA electrode (trademark of De Nora Permelec Ltd.), and $La_{1-x}Sr_xFeO_{3-\delta}$ sintered electrode, which is recently developed at Doshisha University. Oxide-based anodes are preferable. Oxide-based anodes are less likely to be consumed by oxidation reactions.

When applying a voltage, a gas containing carbon dioxide may be added to the molten salt. The gas containing carbon dioxide (hereinafter sometimes referred to as $CO_2$ gas) in a gaseous state is brought into contact with the molten salt in a liquid state. The $CO_2$ gas may be blown into the gas phase of the electrolytic bath and brought into contact with the liquid surface of the molten salt, or the $CO_2$ gas may be blown into the molten salt. The $CO_2$ gas may be a mixed gas of $CO_2$ and an inert gas (typically, argon). A sufficient amount of the $CO_2$ gas may be added to the molten salt before applying a voltage, or the $CO_2$ gas may be added to the molten salt while applying a voltage.

$CO_2$ can be not only physically dissolved in the molten salt but also ionized and dissolved in the electrolytic bath as carbonate ions ($CO_3^{2-}$). $CO_2$, for example, can react with the oxide ions ($O_2^-$) present in the molten salt to form carbonate ions ($CO_3^{2-}$) (see the following formula). $CO_2$ to be added also can be a carbon source of the metal carbide. The oxide ions are derived, for example, from the by-products when the first metal carbide is precipitated.

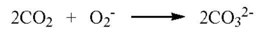

The amount of the $CO_2$ gas to be blown in may be appropriately set depending on the amount of the carbonate of the first metal. The amount of the $CO_2$ gas to be blown in is, for example, the equivalent amount or less of the carbonate of the first metal contained in the molten salt, in consideration of the absorption efficiency of the gas into the molten salt.

The bubble size of the $CO_2$ gas to be blown in is desirably smaller, for promoting the dissolution of $CO_2$ into the molten salt. The bubble size of the $CO_2$ gas is preferably 10 mm or less, more preferably 1 mm or less. The bubble size of the $CO_2$ gas may be 100 nm or more, or may be 1 μm or more. The bubble size of the $CO_2$ gas can be made finer, for example, by bubbling through a porous material made of quartz glass or high-purity alumina, stirring with a stirrer, applying vibration, irradiation with ultrasonic waves, or the like.

The $CO_2$ gas is preferably preheated to a temperature close to that of the molten salt. Preheating can prevent the temperature drop and solidification of the molten salt.

(Metal Carbide)

The metal carbide to be obtained is mainly a carbide of the first metal (first metal carbide). In consideration of the hydrolyzability in the subsequent step, the first metal carbide is preferably at least one selected from the group consisting of $Li_2C_2$, $Na_2C_2$, $K_2C_2$, and $CaC_2$.

In the present disclosure, the first metal carbide can be obtained with high selectivity. The selectivity of the first metal carbide is expressed as the mass of the first metal carbide relative to the total mass of the simple substance of the first metal, compounds containing the first metal (including the first metal carbide), and carbon contained in the precipitates on the cathode. The selectivity of the first metal carbide can be 60 mass % or more, or can be 80 mass % or more. The selectivity of the first metal carbide may be 99 mass % or less, or may be 90 mass % or less. In one embodiment, the selectivity of the first metal carbide is 90 mass % or more and 99.9 mass % or less.

Examples of the compounds containing the first metal other than the first metal carbide include salts of the first metal and the second anion (for example, halides of the first metal), carbonates of the first metal, oxides of the first metal, hydrides of the first metal, and peroxides of the first metal.

(Impurities)

The precipitates may contain impurities. The impurities are precipitates of substances other than the first metal carbide. Examples of the impurities contained in the precipitates on the cathode include at least one selected from the group consisting of carbon, a solidified electrolyte (other metal salt), a compound containing a metal material constituting a device such as an electrode material, minor component contained in the molten salt or the oxide of the first metal, simple substance of the first metal, a compound containing a first metal not included in the target first metal carbide, and a compound containing the second metal.

The carbon may include at least one selected from the group consisting of nanocarbon materials such as graphite, amorphous carbon, glassy carbon, carbon nanotube, diamond, nano diamond, and graphene. Examples of the compound containing the second metal include at least one selected from the group consisting of the simple substance, halide, carbonate, oxide, and carbide of the second metal. Examples of the compound containing a metal material constituting a device include at least one selected from the group consisting of the halides, oxides, carbonates, simple substance of said metal, and their hydrates.

For example, when the first metal is Na, a mixture of NaF and NaCl is used as the other metal salt, and a constituent of the device contains nickel, the precipitates may contain at least one selected from the group consisting of Na, NaCl, $Na_2CO_3$, Ni, $NiCl_2$, as an impurity.

The amount of impurities is preferably 40 mass % or less, more preferably 20 mass % or less, particularly preferably 10 mass % or less, in all precipitates on the cathode. The amount of impurities may be 10 mass % or more, 1 mass % or more, or 0.1 mass % or more, in all precipitates. In one embodiment, the amount of impurities is 0.1 mass % or more and 10 mass % or less, in all precipitates.

The presence of the first metal carbide, the simple substance of the first metal, the compound containing the first metal, and other impurities can be confirmed and quantified, for example, by Raman spectroscopy and X-ray diffraction (XRD) analysis of the precipitates.

[Method for Producing Hydrocarbon]

Figure 2:
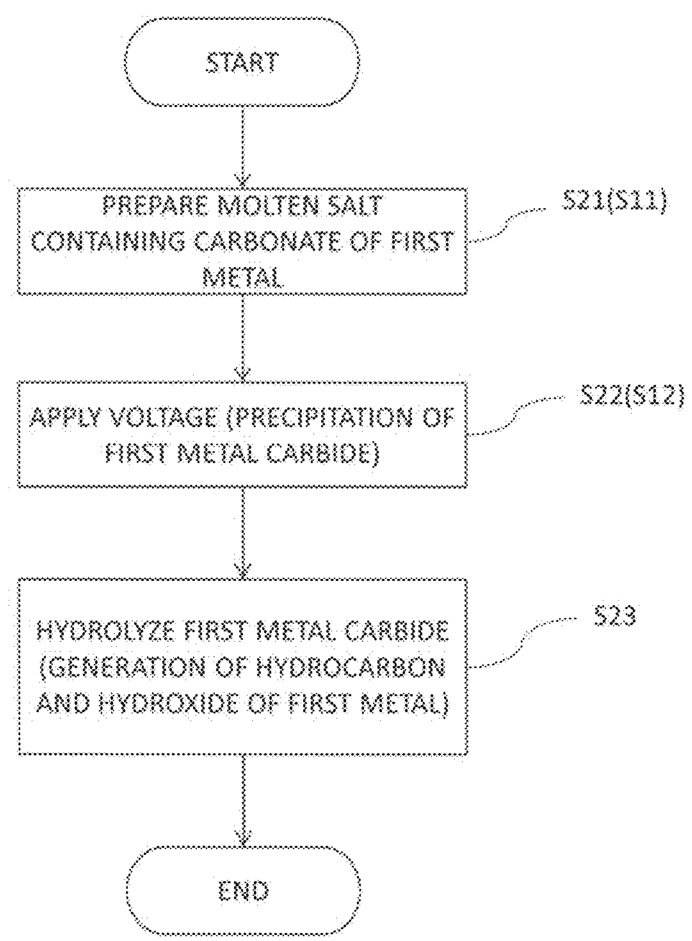
FIG. 2 is a flowchart showing a method for producing a hydrocarbon according to the present disclosure.

The present disclosure includes a method for producing a hydrocarbon from a metal carbide. The method for producing a hydrocarbon in the present disclosure comprises: preparing a molten salt containing a carbonate of a first metal; applying a voltage to the molten salt to obtain precipitates containing a carbide of the first metal; and hydrolyzing the carbide of the first metal to obtain a hydrocarbon and a hydroxide of the first metal. FIG. 2 is a flowchart showing the method for producing a hydrocarbon according to the present disclosure.

(1) Preparation of Molten Salt (S21)

In the same manner as in "Preparation of molten salt (S11)" of the method for producing a metal carbide described above, a molten salt is prepared.

(2) Application of Voltage (S22)

In the same manner as in "Application of voltage (S12)" of the method for producing a metal carbide described above, a voltage is applied to the molten salt. This produces precipitates containing the first metal carbide.

(3) Hydrolysis of Metal Carbide (S23)

Water is brought into contact with the first metal carbide for hydrolysis. This generates a gas containing the target hydrocarbon. Hydrocarbons usually have low solubility in water. The generated hydrocarbon is rapidly exhausted into the gas phase and recovered.

The first metal carbide may be isolated from the precipitates for hydrolysis. Isolation is performed, for example, by a method of pulverizing the precipitates and using the difference in specific gravity. Alternatively, the precipitates may be hydrolyzed, as they are. The carbide of the second metal that may be contained in the precipitates is also hydrolyzed, to generate a hydrocarbon.

Examples of the hydrocarbon to be obtained include methane, ethane, ethylene, acetylene ($C_2H_2$), propane, propylene, butane, and butene. When using the first metal carbide isolated, or when a small amount of impurities (in particular, the simple substance of a metal) are contained in the precipitates, acetylene is obtained as a main component. The main component is a component that accounts for 50 mass % or more of the total mass of the gas to be recovered. Acetylene is an industrially important hydrocarbon.

The gas to be obtained may contain water vapor, hydrogen, nitrogen, and oxygen, as impurities, other than the hydrocarbon. The amount of impurities is preferably 10 mass % or less, more preferably 1 mass % or less, in the gas to be recovered. The amount of impurities may be 0.0001 mass % or more, or 0.001 mass % or more, in the gas to be recovered. In one embodiment, the amount of impurities is 0.0001 mass % or more and 1 mass % or less in the gas to be recovered.

The gas to be recovered, for example, may contain acetylene and at least one selected from the group consisting of ethylene, ethane, methane, and hydrogen.

The presence of the hydrocarbon and impurities can be confirmed and quantified, for example, by gas chromatograph mass spectrometry (GC-MS analysis), Fourier transform infrared absorption spectroscopy (FT-IR analysis) with gas cell, or ultraviolet-visible absorption spectroscopy (UV-Vis analysis) of the gas to be recovered.

In the present disclosure, the Faraday efficiency e for the generation of the hydrocarbon is improved. The Faraday efficiency e may be, for example, 50% or more, or 80% or more. The Faraday efficiency e may be, for example, 99.9% or less, or 99% or less. In one embodiment, the Faraday efficiency e is 50% or more and 99.9% or less.

For example, the Faraday efficiency e for the generation of $C_2H_2$ can be calculated, as follows.

First, the volume proportion of $C_2H_2$ contained in the gas recovered is calculated from the total area of the peaks obtained from the GC-MS analysis and the calibration curve. Next, the volume of $C_2H_2$ generated is calculated from the volume occupied by the gas phase in the recovery container and the volume proportion of $C_2H_2$ in each gas calculated. Finally, assuming that the $C_2H_2$ generated was in standard conditions (0° C., 101 kPa), the Faraday efficiency e (%) is calculated by the following formula.

$$e[\%] = \frac{\text{Actually measured amount of C2H2 produced [mol]}}{\text{Theoretical amount of C2H2 produced, determined from electricity quantity [mol]}} \times 100 = \frac{\dfrac{\text{Calculated volume of C2H2 produced [L]}}{\text{Volume of C2H2 in standard state (22.4)[L/mol]}}}{\dfrac{\text{Average current value during electrolysis } [A] \times \text{electrolysis time } [s]}{\text{Faraday constant (96485)[C/mol]} \times \text{Number of electrons in C2H2(10)[−]}}} \times 100$$

The amount of water to be brought into contact with the precipitates is appropriately set depending on the mass of the precipitates. The amount of water is, for example, equal to or more than the amount necessary for hydrolysis of the metal carbide and the metal contained in the precipitates. In addition, it is desirable to use the amount of water that can immerse the entire precipitates and determined in consideration of evaporation due to heat during hydrolysis. It is desirable to use an amount of water or more than that capable of dissolving all hydroxides to be generated since the hydroxide of the first metal is easily recovered. Use of an excess amount of water tends to increase the load to recover the hydroxide of the first metal. When the first metal is lithium, it may be, for example, 10 times or more, or 20 times or more the mass of the precipitates. The amount of water may be, for example, 100 times or less, or 50 times or less the mass of the precipitates.

The hydroxide of the first metal is generated by the hydrolysis of the first metal carbide together with the hydrocarbon. For example, when sodium carbide is hydrolyzed, sodium hydroxide is generated together with acetylene.

$$Na_2C_2 + 2H_2O \longrightarrow C_2H_2 + 2NaOH$$

(Recycling System)

The present disclosure further comprises recovering, as a carbonate, the hydroxide of the first metal generated, to reuse for producing the first metal carbide as a metal source. This allows hydrocarbons to be produced in a cyclical method.

Figure 3:
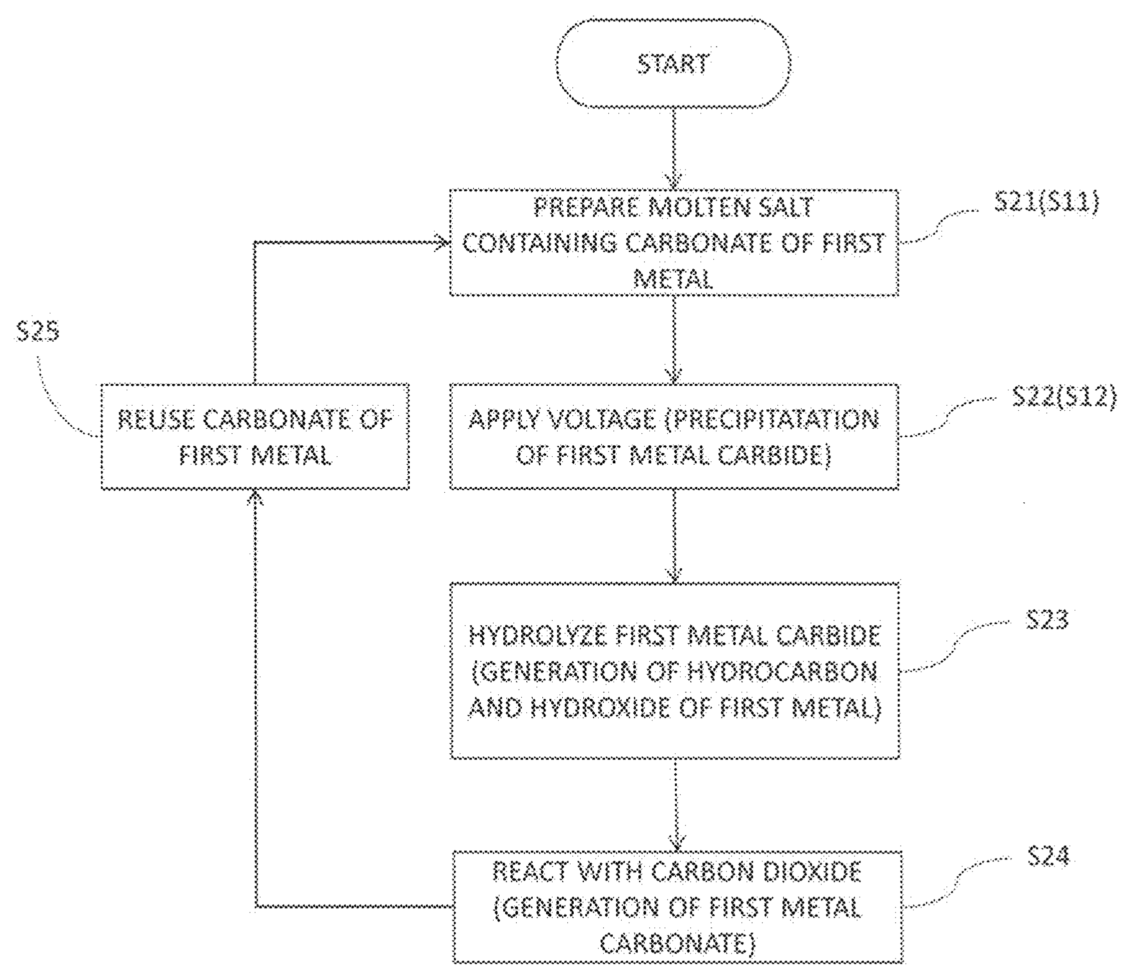
FIG. 3 is a flowchart showing another method for producing a hydrocarbon according to the present disclosure.

The method for producing a hydrocarbon of the present disclosure further comprises: obtaining a carbonate of the first metal by reacting a hydroxide of the first metal generated with carbon dioxide; and reusing the carbonate of the first metal obtained for preparing the molten salt in (1) above. FIG. 3 is a flowchart showing another method for producing a hydrocarbon (recycling system) according to the present disclosure.

(4) Reaction with Carbon Dioxide (S24)

The hydroxide of the first metal is reacted with carbon dioxide. For example, a carbon dioxide gas is blown into the water used for hydrolysis and brought into contact with the hydroxide of the first metal. This produces carbonates of the first metal. For example, when sodium hydroxide is reacted with carbon dioxide, sodium carbonate and water are generated.

$$2NaOH + CO_2 \longrightarrow Na_2CO_3 + H_2O$$

Depending on the solubility in water, the hydroxide of the first metal is settled or dissolved in water used for hydrolysis. The impurities contained in the precipitates are also settled or dissolved in water. The impurities are desirably removed as much as possible, before or after the reaction between the hydroxide of the first metal and carbon dioxide.

When the solubility S of the hydroxide of the first metal in water at 20° C. is 10 g/100 g $H_2O$ or more, (i) the impurities (typically, carbon) settled in water are first removed by filtration or centrifugation. Next, (ii) carbon dioxide is blown into the remaining filtrate, to generate the first metal as a carbonate.

For example, the solubility S of sodium hydroxide is 109 g/100 g $H_2O$. When the first metal is sodium, the impurities settled are first removed by filtration. Thereafter, carbon dioxide is blown into the filtrate, then sodium carbonate is obtained by the following reaction formula.

$$Na(OH)_2 + CO_2 \longrightarrow NaCO_3 + H_2O$$

The solubility S of sodium carbonate is 21.5 g/100 g $H_2O$. Solidified sodium carbonate can be obtained efficiently by removing water from the filtrate. Metal carbonates with low solubility into water (for example, lithium carbonate) can be recovered as sediments.

Examples of the first metal with a solubility S of the hydroxide of 10 g/100 g $H_2O$ or more include lithium, potassium, rubidium, and cesium, other than sodium.

When the solubility S of the hydroxide of the first metal is less than 10 g/100 g $H_2O$, and the first metal can form a bicarbonate, (a) the bicarbonate of the first metal may be once generated by blowing an excess amount of $CO_2$ into water containing the hydroxide of the first metal. The bicarbonate of the first metal is usually easily dissolved in water. Then, (b) the sediment containing impurities is removed in the same manner as in (i) above. The remaining aqueous solution is heated to pyrolyze the bicarbonate of the first metal and the hydroxide of the first metal is regenerated. Finally, the hydroxide of the first metal is again brought into contact with $CO_2$, to generate the first metal as a carbonate.

For example, the solubility S of calcium hydroxide ($Ca(OH)_2$) is 0.17 g/100 g $H_2O$, and calcium forms a bicarbonate. Calcium carbonate ($CaCO_3$) can be obtained from calcium hydroxide ($Ca(OH)_2$) through calcium bicarbonate ($Ca(HCO_3)_2$) and calcium hydroxide ($Ca(OH)_2$) by the following reaction formula. $CO_2$ generated by pyrolysis of calcium bicarbonate can be reused for this processing.

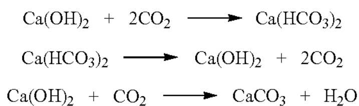

$$Ca(OH)_2 + 2CO_2 \longrightarrow Ca(HCO_3)_2$$
$$Ca(HCO_3)_2 \longrightarrow Ca(OH)_2 + 2CO_2$$
$$Ca(OH)_2 + CO_2 \longrightarrow CaCO_3 + H_2O$$

The amount of $CO_2$ gas to be blown in may be appropriately set depending on the amount of the hydroxide of the first metal. The amount of $CO_2$ gas to be blown in is not limited, and may be, for example, the equivalent amount or more of the hydroxide of the first metal contained in an aqueous solution, in consideration of the absorption efficiency of the gas into the aqueous solution.

The bubble size of the $CO_2$ gas to be blown in is desirably smaller, for efficiently reacting $CO_2$ that is a gas with the hydroxide of the first metal. The bubble size of the $CO_2$ gas is preferably 10 mm or less, more preferably 1 mm or less. The bubble size of the $CO_2$ gas may be 100 nm or more, or may be 1 μm or more.

The product containing the carbonate of the first metal can contain the oxide of the second metals, hydroxides, peroxides, carbonates, bicarbonates, and their hydrates of the first and second metals as impurities. The amount of impurities is preferably 20 mass % or less, more preferably 10 mass % or less, of the total amount of the aforementioned product. The amount of impurities may be 0.1 mass % or more, or 1.0 mass % or more, of the total amount of the product. In one embodiment, the amount of impurities is 0.1 mass % or more and 20 mass % or less of the total amount of the product. When the amount of impurities falls within such a range, side reactions in the reuse process (for example, precipitation process of the first metal carbide) can be easily suppressed, to further improve the Faraday efficiency. The presence of the oxide of the first metal and impurities can be confirmed and quantified, for example, by Raman spectroscopy and X-ray diffraction (XRD) analysis of the precipitates.

(5) Reuse of Carbonate of First Metal (S25)

The carbonate of the first metal obtained is reused for preparing the molten salt of (1) above. This gives a cycle including the production of the first metal carbide using the carbonate of the first metal and the production of the hydrocarbon using the first metal carbide. The product, which may contain impurities, may be reused.

[Metal Carbide Composition]

The present disclosure includes a metal carbide composition. The metal carbide composition comprises a carbide of the first metal as a main component and at least one selected from the group consisting of carbon, the simple substance, halide, carbonate, oxide, hydride, and peroxide of the first metal, and the simple substance, halide, carbonate, oxide, and carbide of a metal other than the first metal. The metal carbide composition is obtained, for example, by the method for producing a metal carbide of the present disclosure. The metal carbide composition is a precipitate generated on the cathode. Examples of the metal other than the first metal include the second metal.

The main component of the metal carbide composition is the carbide of the first metal. The first metal is as described above. The main component means a component that accounts for 50 mass % or more of the total mass of the metal carbide composition. The content ratio of the first metal carbide is preferably 80 mass % or more, more preferably 90 mass % or more, of the mass of the metal carbide composition. The content ratio of the first metal carbide may be 99.9 mass % or less, or 99 mass % or less, of the mass of the metal carbide composition. In one embodiment, the content ratio of the first metal carbide is 80 mass % or more and 99.9 mass % or less of the mass of the metal carbide composition.

Also when the metal carbide composition is obtained by the method for producing a metal carbide of the present disclosure, the metal carbide composition contains at least one selected from the group consisting of carbon, the simple substance, halide, carbonate, oxide, hydride, and peroxide of the first metal, and the simple substance, halide, carbonate, oxide, and carbide of the second metal, together with the first metal carbide. Other than above, the metal carbide composition may contain at least one selected from the group consisting of a solidified electrolyte (other metal salt), the halide, oxide, metal of the material constituting a device, and their hydrates. The carbon may contain at least one selected from the group consisting of a nanocarbon material such as graphite, amorphous carbon, glassy carbon, carbon nanotube, diamond, nanodiamond, and graphene.

EXAMPLES

Example 1

(Production of Metal Carbide)

NaF and NaCl were mixed so as to be NaF/NaCl=34 mol %/66 mol %, followed by vacuum drying at 200° C., 100 Pa or less for 24 hours or more. 1 mol % of $Na_2CO_3$ relative to the total number of moles of NaCl and NaF was weighed, and a mixed salt was obtained in addition to the aforementioned mixture. The mixed salt was accommodated in a high-purity alumina container and set in an electric furnace, and the mixed salt was heated to 700° C. Thus, a molten salt of NaCl—NaF—$Na_2Co_3$ was obtained.

Then, a working electrode (nickel plate of 1 cm×1.5 cm), a counter electrode (platinum coil), and a reference electrode ($Ag^+/Ag$) were attached to the lid of the container, and the container was sealed with the lid. The molten salt in the container was heated to 700° C., and $CO_2$ was blown in at a flow rate of 100 mL/minute for 30 minutes or more. Subsequently, a voltage was applied for 30 minutes, while the potential of the working electrode relative to the reference electrode was maintained at 0.5 V using a potentiogalvanostat. Thereafter, the working electrode was taken out to collect the precipitates on the surface, and it was subjected to XRD analysis. All experimental operations were performed in a glovebox containing a high-purity argon atmosphere.

Figure 4:
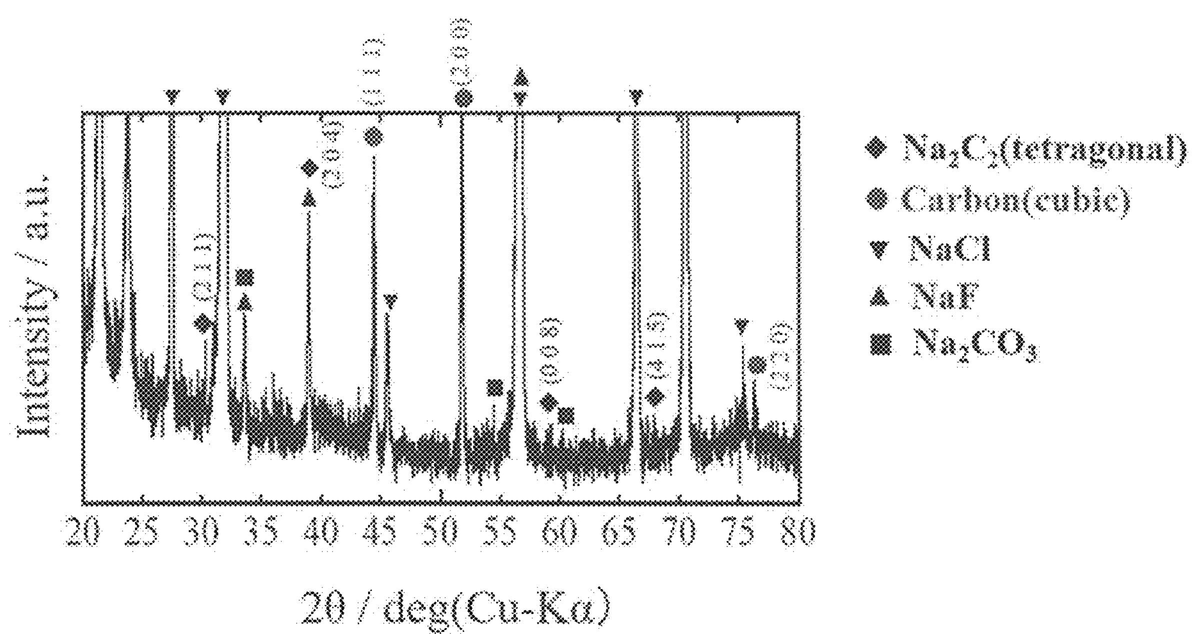
FIG. 4 is a graph showing the results of the XRD analysis of the precipitates obtained in Example 1.

FIG. 4 shows the results of the XRD analysis. This analysis demonstrated that the precipitates contained $Na_2C_2$ as the main component, and contained NaCl, NaF, $Na_2CO_3$, and carbon, as impurities. The mass proportion of the impurities in the precipitates was sufficiently less than 50 mass %. The mass proportion of the impurities was calculated from the peak intensity ratio by XRD analysis.

(Production of Hydrocarbon)

A small amount of pure water was added to the precipitates accommodated in the sealed test tube at normal temperature)(23° ° C., so that the precipitates was hydrolyzed. The total amount of water added was 2.5 ml. Bubbling was confirmed in the test tube, and then the test tube was left standing until no bubbling was observed. Subsequently, 100 μl (micro liter) of the gas in the test tube was collected using a gastight syringe.

The gas obtained were subjected to GC-MS analysis using a gas chromatograph (GC) device, and the GC-MS analysis demonstrated $C_2H_2$ was generated as the main component. Furthermore, it revealed that ethane and hydrogen were generated as by-products. Other than above, water, carbon dioxide, nitrogen, oxygen, and argon were contained as impurities. In addition, the amount of each component generated was confirmed. The mass proportion of $C_2H_2$ in the recovered gas was sufficiently greater than 50 mass %.

(Reproduction of Metal Carbonate)

The liquid remaining after the hydrolysis was filtered, to remove the sediment. Next, carbon dioxide was blown into the filtrate. Thereafter, water was removed to obtain a solidified matter. This solidified matter was subjected to XRD analysis, to confirm the reproduction of $Na_2CO_3$ as the main component. The solidified matter contained $NaHCO_3$ as an impurity. The mass proportion of $Na_2CO_3$ in the solidified matter obtained was 90 mass % or more, and the mass proportion of the impurity was 10 mass % or less.

Example 2

(Production of Metal Carbide)

Figure 5:
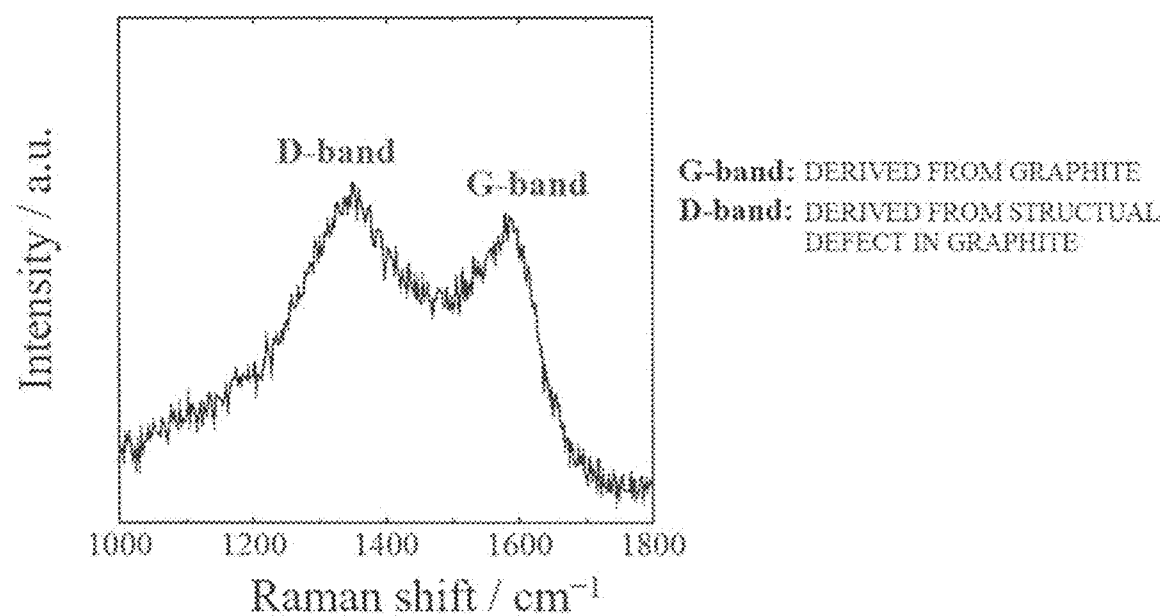
FIG. 5 is a graph showing the results of the Raman spectroscopy of the precipitates obtained in Example 2.

Precipitates were obtained in the same manner as in Example 1, except that a glass container was used as a container to accommodate the mixed salt, and a voltage was applied for 30 minutes, while the potential of the working electrode relative to the reference electrode was maintained at 0.7 V. FIG. 5 shows the results of the Raman spectroscopy analysis of the precipitates obtained. This analysis demonstrated that the precipitates contained $Na_2C_2$ as the main component, and contained NaCl, NaF, $Na_2CO_3$, and carbon, as impurities. The mass proportion of the impurities in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$ as the main component. Furthermore, it revealed that ethane and hydrogen were generated as by-products. Other than above, water, carbon dioxide, nitrogen, oxygen, and argon were contained as impurities. The mass proportion of $C_2H_2$ in the recovered gas was sufficiently greater than 50 mass %.

(Reproduction of Metal Carbonate)

A solidified matter was obtained in the same manner as in Example 1. The XRD analysis of the solidified matter obtained demonstrated that the solidified matter contained $Na_2CO_3$ as the main component, and contained $NaHCO_3$ as an impurity. The mass proportion of $Na_2CO_3$ in the solidified matter obtained was 90 mass %, and the mass proportion of the impurity was 10 mass %.

Example 3

(Production of Metal Carbide)

LiCl, KCl, and $CaCl_2$) were mixed so as to be LiCl/KCl/$CaCl_2$)=52.3 mol %/11.6 mol %/36.1 mol %, followed by vacuum drying at 200° ° C. and 100 Pa or less for 24 hours or more. 1 mol % of $CaCO_3$ relative to the total of number of moles of LiCl, KCl, and $CaCl_2$) was weighed and added to the aforementioned mixture, to obtain a mixed salt. The mixed salt was accommodated in a PYREX (trademark of Corning Incorporated) container and set in an electric furnace, to heat the mixed salt to 450° C. Thus, a molten salt of LiCl—KCl—$CaCl_2$)—$CaCO_3$ was obtained.

Precipitates were obtained in the same manner as in Example 1, except that the molten salt was used, and a voltage was applied for 30 minutes, while the potential of the working electrode relative to the reference electrode was maintained at 0.1 V.

Figure 6:
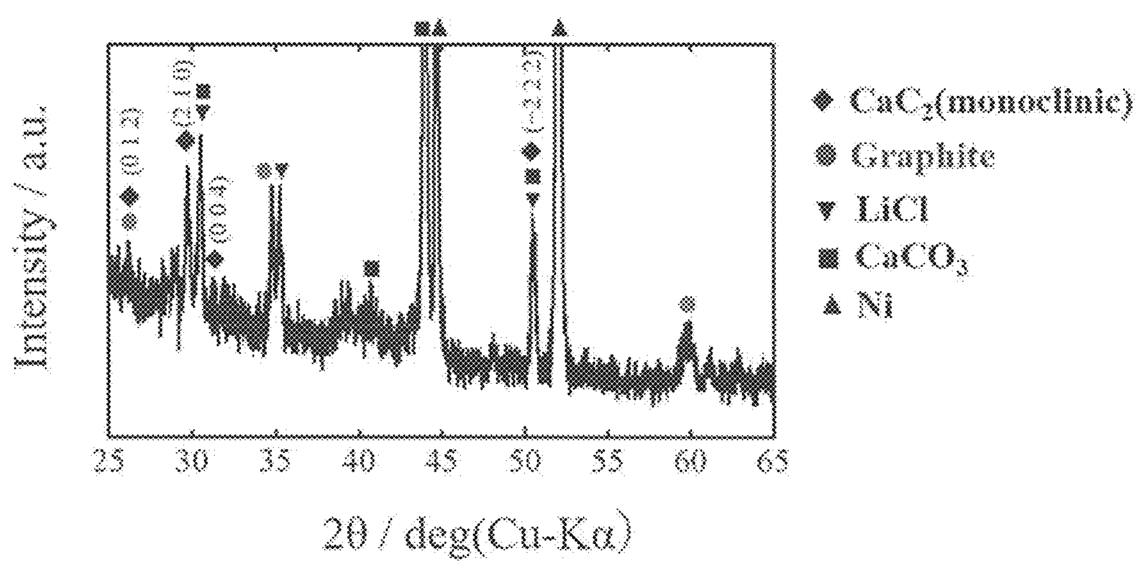
FIG. 6 is a graph showing the results of the XRD analysis of the precipitates obtained in Example 3.

FIG. 6 shows the results of the XRD analysis of the precipitates obtained. This analysis demonstrated that the precipitates contained $CaC_2$, and LiCl and graphite, as impurities. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$ as the main component. Furthermore, it revealed that ethane and hydrogen were generated as by-products. Other than above, water, carbon dioxide, nitrogen, oxygen, and argon were contained as impurities. The mass proportion of $C_2H_2$ in the recovered gas was sufficiently greater than 50 mass %.

(Reproduction of Metal Carbonate)

A solidified matter was obtained in the same manner as in Example 1. The XRD analysis of the solidified matter obtained demonstrated that the solidified matter contained $CaCO_3$ as the main component, and contained $Ca(OH)_2$ as an impurity. The mass proportion of $CaCO_3$ in the solidified matter obtained was 95 mass % or more, and the mass proportion of the impurity was 5 mass % or less.

Example 4

(Production of Metal Carbide)

LiCl, KCl, and $CaCl_2$) were mixed so as to be LiCl/KCl/$CaCl_2$)=52.3 mol %/11.6 mol %/36.1 mol %, followed by vacuum drying at 200° C. and 100 Pa or less for 24 hours or more. 1 mol % of $CaCO_3$ relative to the total of number of moles of LiCl, KCl, and $CaCl_2$) was weighed and added to the mixture, to obtain a mixed salt. The mixed salt was accommodated in a PYREX (trademark of Corning Incorporated) container and set in an electric furnace, to heat the mixed salt to 450° C. Thus, a molten salt of LiCl—KCl—$CaCl_2$)—$CaCO_3$ was obtained.

Then, a working electrode (nickel plate of 1 cm×1 cm), a counter electrode (platinum coil), and a reference electrode ($Ag^+$/Ag) were attached to a lid of the container, and the container was sealed with the lid. The molten salt in the container was heated to 450° ° C., and Ar was blown therein at a flow rate of 100 mL/minute for 30 minutes or more. Subsequently, a voltage was applied for 30 minutes, while the potential of the working electrode relative to the reference electrode was maintained at 1.3 V using a potentiogalvanostat. Thereafter, the working electrode was taken out to collect the precipitates on the surface for XRD analysis. All experimental operations were performed in a glovebox containing a high-purity argon atmosphere.

Figure 7:
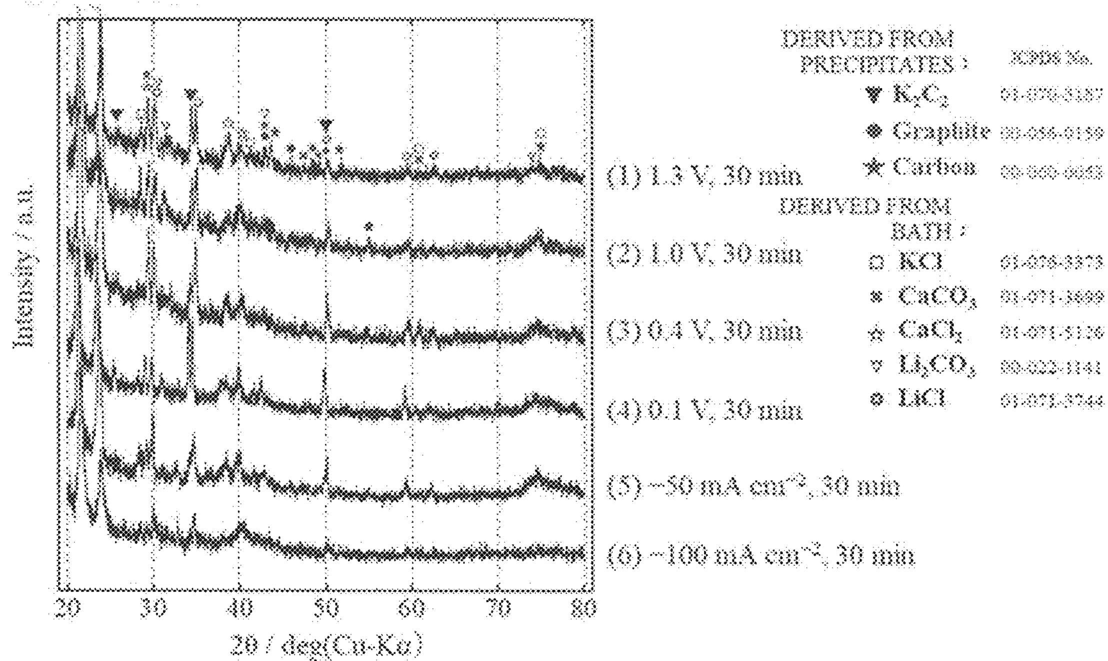
FIG. 7 is a graph showing the results of the XRD analysis of the precipitates obtained in Example 4 to 9.

FIG. 7(1) shows the results of the XRD analysis of the precipitates obtained. This analysis demonstrated that the precipitates contained $K_2C_2$ as the main component, and contained graphite, carbon, bath-derived KCl, $CaCO_3$, $CaCl_2$), $Li_2CO_3$, and LiCl, as impurities. The mass proportion of the impurities in the precipitates was sufficiently less than 50 mass %.

Example 5

(Production of Metal Carbide)

Precipitates were obtained in the same manner as in Example 4, except that a voltage was applied for 30 minutes, while the potential of the working electrode relative to the reference electrode was maintained at 1.0 V using a potentio-galvanostat.

FIG. 7(2) shows the results of the XRD analysis of the precipitates obtained. This analysis demonstrated that the precipitates contained $K_2C_2$ as the main component, and contained graphite, carbon, bath-derived KCl, $CaCO_3$, $CaCl_2$), $Li_2CO_3$, and LiCl, as impurities. The mass proportion of the impurities in the precipitates was sufficiently less than 50 mass %.

Example 6

(Production of Metal Carbide)

Precipitates were obtained in the same manner as in Example 4, except that a voltage was applied for 30 minutes, while the potential of the working electrode relative to the reference electrode was maintained at 0.4 V using a potentio-galvanostat.

FIG. 7(3) shows the results of the XRD analysis of the precipitates obtained. This analysis demonstrated that the precipitates contained $K_2C_2$ as the main component, and contained graphite, carbon, bath-derived KCl, $CaCO_3$, $CaCl_2$), $Li_2CO_3$, and LiCl, as impurities. The mass proportion of the impurities in the precipitates was sufficiently less than 50 mass %.

(Production of Hydrocarbon)

The precipitates were hydrolyzed in the same manner as in Example 1. It was demonstrated that the gas generated contained $C_2H_2$ as the main component. Furthermore, it was revealed that methane and hydrogen were generated as by-products. The mass proportion of $C_2H_2$ in the recovered gas was sufficiently greater than 50 mass %.

Example 7

(Production of Metal Carbide)

Precipitates were obtained in the same manner as in Example 4, except that a voltage was applied for 30 minutes, while the potential of the working electrode relative to the reference electrode was maintained at 0.1 V using a potentio-galvanostat.

FIG. 7(4) shows the results of the XRD analysis of the precipitates obtained. This analysis demonstrated that the precipitates contained $K_2C_2$ as the main component, and contained graphite, carbon, bath-derived KCl, $CaCO_3$, $CaCl_2$), $Li_2CO_3$, and LiCl, as impurities. The mass proportion of the impurities in the precipitates was sufficiently less than 50 mass %.

(Production of Hydrocarbon)

Figure 8:
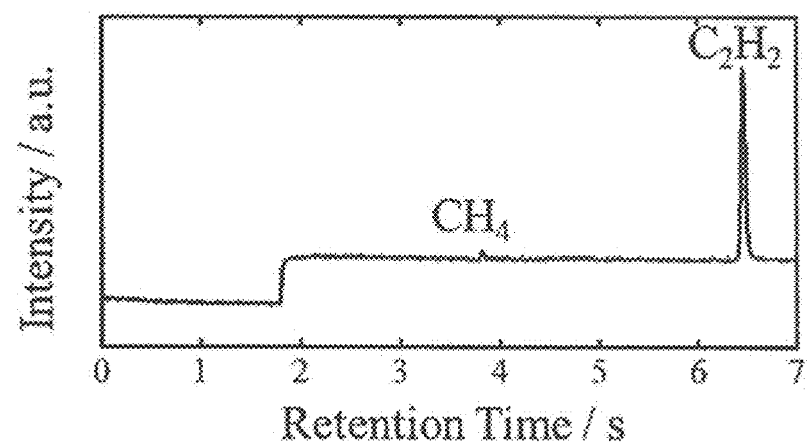
FIG. 8 is a graph showing the results of the GC-MS analysis of the gas generated in Example 7.

The precipitates were hydrolyzed in the same manner as in Example 1. FIG. 8 shows the results of the GC-MS analysis of the gas generated. These results demonstrated that the gas generated contained $C_2H_2$ as the main component. Furthermore, they revealed that methane and hydrogen were generated as by-products. The mass proportion of $C_2H_2$ in the recovered gas was sufficiently greater than 50 mass %.

Example 8

(Production of Metal Carbide)

Precipitates were obtained in the same manner as in Example 4, except that a voltage was applied for 30 minutes, while the current value between the working electrode and the counter electrode was maintained at 100 mA, that is, the current density of the working electrode was maintained at 50 mA/cm$^2$, using a potentio-galvanostat. The potential of the working electrode relative to the reference electrode was about 0 V.

FIG. 7(5) shows the results of the XRD analysis of the precipitates obtained. This analysis demonstrated that the precipitates contained $K_2C_2$ as the main component, and contained graphite, carbon, bath-derived KCl, $CaCO_3$, $CaCl_2$), $Li_2CO_3$, and LiCl, as impurities. The mass proportion of the impurities in the precipitates was sufficiently less than 50 mass %.

(Production of Hydrocarbon)

Figure 9:
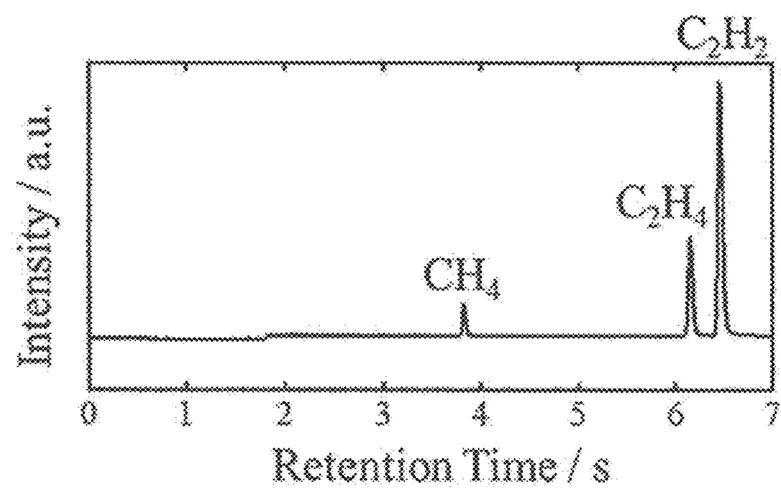
FIG. 9 is a graph showing the results of the GC-MS analysis of the gas generated in Example 8.

The precipitates were hydrolyzed in the same manner as in Example 1. FIG. 9 shows the results of the GC-MS analysis of the gas generated. The results demonstrated that the gas generated contained $C_2H_2$ and ethylene. Furthermore, they revealed that methane and hydrogen were generated as by-products. The mass proportion of $C_2H_2$ in the recovered gas was sufficiently greater than 50 mass %. The results of the GC-MS analysis demonstrated that the Faraday efficiency for the $C_2H_2$ gas generation was calculated to be about 12%.

Example 9

(Production of Metal Carbide)

Precipitates were obtained in the same manner as in Example 4, except that a voltage was applied for 30 minutes, while the current value between the working electrode and the counter electrode was maintained at 200 mA, that is, the current density of the working electrode was maintained at 100 mA/cm$^2$, using a potentio-galvanostat. The potential of the working electrode relative to the reference electrode was about 0 V.

FIG. 7(6) shows the results of the XRD analysis of the precipitates obtained. This analysis demonstrated that the precipitates contained $K_2C_2$ as the main component, and contained graphite, carbon, bath-derived KCl, $CaCO_3$, $CaCl_2$), $Li_2CO_3$, and LiCl, as impurities. The mass proportion of the impurities in the precipitates was sufficiently less than 50 mass %.

(Production of Hydrocarbon)

Figure 10:
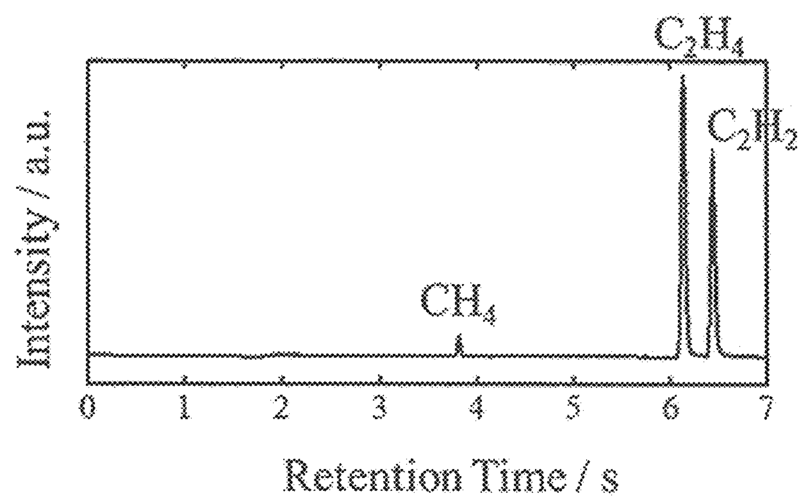
FIG. 10 is a graph showing the results of the GC-MS analysis of the gas generated by hydrolyzing the precipitates obtained in Example 9.

The precipitates were hydrolyzed in the same manner as in Example 1. FIG. 10 shows the results of the GC-MS analysis of the gas generated. The results demonstrated that the gas generated contained $C_2H_2$ and ethylene. Furthermore, they revealed that methane and hydrogen were generated as by-products.

The present disclosure further includes the following embodiments.

[1] A method for producing a metal carbide, comprising: preparing a molten salt containing a carbonate of a first metal; and obtaining precipitates containing a first metal carbide by applying a voltage to the molten salt.

[2] The method for producing a metal carbide according to [1] above, wherein the molten salt further contains a halide of a second metal.

[3] The method for producing a metal carbide according to [2] above, wherein the first metal and the second metal are the same.

[4] The method for producing a metal carbide according to [2] or [3] above, wherein halogen in the halide contains chlorine.

[5] The method for producing a metal carbide according to [2] or [3] above, wherein the halogen in the halide contains fluorine.

[6] The method for producing a metal carbide according to any one of [1] to [5] above, wherein the precipitates further contain at least one selected from the group consisting of carbon, the simple substance, halide, carbonate, oxide, hydride, and peroxide of the first metal, and the simple substance, halide, carbonate, oxide, and carbide of a metal other than the first metal contained in the molten salt.

[7] The method for producing a metal carbide according to any one of [1] to [6] above, wherein the first metal contains at least one selected from the group consisting of alkali metals and alkaline earth metals.

[8] The method for producing a metal carbide according to any one of [1] to [7] above, wherein the first metal contains at least one selected from the group consisting of lithium, sodium, potassium, and calcium.

[9] A method for producing a hydrocarbon, comprising: preparing a molten salt containing a carbonate of a first metal; obtaining precipitates containing a first metal carbide by applying a voltage to the molten salt; and obtaining a gas containing a hydrocarbon and a hydroxide of the first metal by hydrolyzing the first metal carbide.

[10] The method for producing a hydrocarbon according to [9] above, further comprising: obtaining the carbonate of the first metal by reacting the hydroxide with carbon dioxide; and reusing the oxide obtained for preparing the molten salt.

[11] The method for producing a hydrocarbon according to [9] or [10] above, wherein the hydrocarbon is acetylene.

[12] The method for producing a hydrocarbon according to any one of [9] to [11] above, wherein the gas contains acetylene and at least one selected from the group consisting of ethylene, ethane, methane, and hydrogen.

[13] A metal carbide composition comprising: a first metal carbide as the main component; and further at least one selected from the group consisting of carbon, the simple substance, halide, carbonate, oxide, hydride, and peroxide of the first metal, and the simple substance, halide, carbonate, oxide, and carbide of a metal other than the first metal.

INDUSTRIAL APPLICABILITY

The production method of the present disclosure is useful in various fields, since the reaction rapidly proceeds at a relatively low temperature.

The invention claimed is:

1. A method for producing a hydrocarbon, comprising:
preparing a molten salt containing a carbonate of a first metal;
obtaining precipitates containing a first metal carbide by applying a voltage to the molten salt; and
obtaining a gas containing the hydrocarbon and a hydroxide of the first metal by hydrolyzing the first metal carbide.

2. The method for producing a hydrocarbon according to claim 1, further comprising:
obtaining the carbonate of the first metal by reacting the hydroxide with carbon dioxide; and
reusing the carbonate obtained for preparing the molten salt.

3. The method for producing a hydrocarbon according to claim 1, wherein the hydrocarbon is acetylene.

4. The method for producing a hydrocarbon according to claim 1, wherein the gas contains acetylene and at least one selected from the group consisting of ethylene, ethane, methane, and hydrogen.

* * * * *